US006998364B2

(12) United States Patent
Bernard et al.

(10) Patent No.: US 6,998,364 B2
(45) Date of Patent: *Feb. 14, 2006

(54) PROCESS FOR THE FORMATION OF URETHANE VIA TRANSCARBAMATION

(75) Inventors: Jean-Marie Bernard, Mornant (FR); Bernard Jousseaume, Talence (FR); Christian Laporte, Castanet-Tolosan (FR); Thierry Toupance, Talence (FR)

(73) Assignee: Rhodia Chimie, Boulogne Billancourt (FR)

( * ) Notice: Subject to any disclaimer, the term of this patent is extended or adjusted under 35 U.S.C. 154(b) by 55 days.

This patent is subject to a terminal disclaimer.

(21) Appl. No.: 10/398,836

(22) PCT Filed: Oct. 11, 2001

(86) PCT No.: PCT/FR01/03144

§ 371 (c)(1),
(2), (4) Date: Apr. 9, 2003

(87) PCT Pub. No.: WO02/31014

PCT Pub. Date: Apr. 18, 2002

(65) Prior Publication Data

US 2004/0044242 A1    Mar. 4, 2004

(30) Foreign Application Priority Data

Oct. 13, 2000  (FR)  .................................. 00 13161
Oct. 13, 2000  (FR)  .................................. 00 13162

(51) Int. Cl.
*B01J 31/00* (2006.01)
(52) U.S. Cl. .................... 502/150; 560/24; 560/115; 560/157; 524/589
(58) Field of Classification Search ............... 502/150; 560/24, 115, 157; 524/589
See application file for complete search history.

(56) References Cited

U.S. PATENT DOCUMENTS

| 4,018,744 A | | 4/1977 | Wolgemuth ............ 260/77.5 B |
| 4,279,833 A | * | 7/1981 | Culbertson et al. ......... 558/393 |
| 4,386,033 A | | 5/1983 | Konig et al. ................. 260/453 |
| 4,820,830 A | * | 4/1989 | Blank .......................... 560/158 |
| 5,206,412 A | | 4/1993 | Rodriguez et al. ............. 560/25 |
| 5,326,815 A | * | 7/1994 | Serdiuk et al. ............. 524/591 |
| 5,373,069 A | * | 12/1994 | Rehfuss et al. .............. 525/456 |
| 5,430,122 A | | 7/1995 | Drysdale ...................... 528/55 |
| 5,527,266 A | | 6/1996 | Hiraishi et al. ................ 602/8 |
| 5,563,208 A | * | 10/1996 | K onig et al. .............. 524/591 |
| 5,665,433 A | * | 9/1997 | Moussa et al. ............. 427/377 |
| 5,792,810 A | * | 8/1998 | Menovcik et al. .......... 524/590 |
| 5,945,499 A | * | 8/1999 | Ohrbom et al. ................ 528/75 |
| 5,976,615 A | * | 11/1999 | Menovcik et al. .......... 427/140 |
| 6,150,465 A | * | 11/2000 | Harris et al. ................. 525/163 |
| 6,258,898 B1 | * | 7/2001 | Rehfuss et al. .............. 525/518 |
| 6,331,596 B1 | * | 12/2001 | Ramesh et al. .......... 525/329.9 |
| 6,391,969 B1 | * | 5/2002 | Harris et al. ................. 525/163 |
| 6,531,560 B1 | * | 3/2003 | Campbell et al. ............ 526/301 |
| 6,602,552 B1 | * | 8/2003 | Daraskevich et al. ..... 427/388.1 |
| 6,642,302 B1 | * | 11/2003 | Wamprecht et al. ......... 524/589 |
| 6,646,049 B1 | * | 11/2003 | Ramesh ....................... 525/111 |
| 6,844,395 B1 | * | 1/2005 | Ohrbom et al. ............. 524/590 |
| 6,939,592 B1 | * | 9/2005 | Lynch et al. ................ 428/35.7 |

FOREIGN PATENT DOCUMENTS

WO   WO 01/00689 A1 * 1/2001
WO   WO 02/30565 A1 * 4/2002

OTHER PUBLICATIONS

Copending U.S. Appl. No. 10/398837, (Bernard et al.).*
Patent Abstracts of Japan, vol. 11, No. 242 (C-438), Aug. 7, 1987 & JP 62048716 A (Nippon Sheet Glass Co Ltd.) Mar. 3, 1987 abstract.
International Search Report.

* cited by examiner

*Primary Examiner*—J. A. Lorengo
*Assistant Examiner*—Jennine Brown

(57) ABSTRACT

The invention concerns a novel catalyst for forming urethanes. Said catalyst is characterized by the general formula: $MY_{3-q}[Z]_q$, wherein: Z is the radical corresponding to the anion of a super acid whereof the Hamett constant is at least equal to 13 and advantageously more than 13, M representing a trivalent metal, preferably known for forming Lewis acids; Y is an anion or a monovalent anionic function; and q is an integer selected advantageously between 1 and 3, inclusively. The invention is applicable to paint.

18 Claims, No Drawings

PROCESS FOR THE FORMATION OF URETHANE VIA TRANSCARBAMATION

This application is an application under 35 U.S.C. Section 371 of International Application Number PCT/FR01/03144 filed on Oct. 11,2001.

A subject matter of the present invention is novel transcarbamation catalysts. The invention relates more specifically to the use of novel catalysts which are not based on tin.

Because of their high reactivity and their relative toxicity, isocyanates are often used in a derived form or in a masked form. This derived form or this masked form exhibits the disadvantage corresponding to its advantages, that is to say that it is not very reactive, and consequently requires the use of catalysts in order for the reaction to be able to take place at temperatures acceptable in industry.

Masked isocyanates can be used in all the applications of isocyanates, namely paints, varnishes and more generally coatings, adhesives, and some specialty polymers.

The most widely used catalysts are dialkyltin alkanoates, the most well known of which is dibutyltin dilaurate. However, for some applications, dibutyltin dilaurate exhibits an insufficient activity and consequently it is necessary to use it at very high concentrations.

These (trans)carbamation catalysts make it possible to prepare polyurethanes, in particular aliphatic polyurethanes.

However, tin salts have a reputation for toxicity which is detrimental to their use and consequently attempts are being made, in numerous applications, to replace them with compounds not exhibiting these disadvantages.

In addition, industry is always on the lookout for compounds having better catalytic activities than the existing catalysts.

The most widely used catalyst as reference in the field of polyurethanes is dibutyltin dilaurate.

One of the aims of the present invention is therefore to provide a carbamation catalyst which is at least as active as dibutyltin dilaurate but which is not based on tin.

Another aim of the present invention is to provide a catalyst which can be used for the synthesis of polyurethanes, in particular polyurethanes of aliphatic nature.

Another aim of the present invention is to provide a catalyst of the preceding type which makes it possible to carry out the synthesis of polyurethane from masked polyisocyanates.

Another aim of the present invention is to provide a catalyst which makes it possible to carry out a transcarbamation resulting in polyurethanes starting from light alkyl carbamates; the term "alkyl" corresponding to an alcohol with a boiling point at normal pressure at most equal to 150° C. (2 significant figures), advantageously at most 100° C. (2 significant figures).

Another aim of the present invention is to provide a catalyst of the preceding type which can be used when the urethanes or polyurethanes are used as binder with the coating (varnishes or paints).

These aims, and others which will become apparent subsequently, are achieved by means of the use as catalyst of compounds corresponding to the following general formula (I):

$$MY_{3-q}[Z]_q,$$

where:

Z is the radical corresponding to the anion of a superacid, the Hammett constant of which is at least equal to 13 and advantageously greater than 13;

M represents a trivalent metal, preferably known for forming Lewis acids;

Y is a monovalent anion or anionic functional group, and;

q is an integer advantageously chosen between 1 and 3, including the limits.

Advantageously, Z is of formula (II):

$$(R_x)-SO_2-\zeta$$

where:

$R_x$ is a fluorine or, advantageously, a radical, the carbon of which carrying the sulfonic functional group is perhalogenated, and $\zeta$ is an oxygen or an atom from Group V, preferably nitrogen, monosubstituted by an electron-withdrawing radical EWG, advantageously by a radical of formula $(R'_x)-SO_2-$, where $R'_x$ is chosen from the same radicals as $R_x$.

EWG may be chosen from the same families as $R_x$, with the same preferences as the latter. It is the same for $R'_x$, $R_x$, $R'_x$ and EWG; these radicals can be identical or different.

$\zeta$ is generally oxygen, to give a formula (I'):

$$MY_{3-q}[(R_x)-SO_2-O-]_q,$$

where:

M represents a trivalent metal, preferably known for forming Lewis acids;

Y is a monovalent anion or anionic functional group, and;

$R_x$ is a fluorine or, advantageously, a radical, the carbon of which carrying the sulfonic functional group is perhalogenated, and q is an integer advantageously chosen between 1 and 3, including the limits.

M is thus the trivalent cation corresponding to an element of metallic nature.

Mention may also be made, among the anions $Z^-$, of the imides of formula (III):

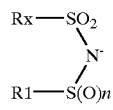

where R1 is a fluorine or organic radical (that is to say, comprising carbon) advantageously comprising at most 30 carbon atoms when it is not polymeric (that is to say, does not constitute a bond for attaching to a polymer) and where n is 1 or 2, advantageously 2, especially if R1 is fluorine.

In particular, $Z^-$ can constitute a compound of formula (IV):

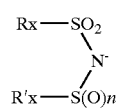

or of formula (V):

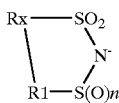

In the case where $R_x$ and R1 are connected, $R_x$ and $R_1$ have to be divalent. It follows, but this goes without saying, that R1 in this case cannot be fluorine.

Very good results are obtained when q is equal to 3. The halogenated carbon is advantageously a perfluorinated carbon and more preferably a perfluoro-methylene group, as will become apparent subsequently. The other anion or the other anions are organic or inorganic anions, preferably monoanions.

Mention may be made, among these anions, of sulfonates, monoalkyl sulfates (when the latter are stable in the medium), carboxylates, halides, halogenates (when the latter are not too oxidizing for the medium), or phosphates, phosphonates and phosphinates, preferably rendered monovalent by partial esterification, when this is necessary; pyrophosphates can be envisaged in the media where they are stable.

However, it is preferable for these anions, other than the perhalogenated sulfonates, not to be chelating.

It is also preferable for the $pK_a$ of the acid associated with these anions to be at most equal to approximately 10, preferably to approximately 5, more preferably to approximately 2.

It is preferable for the associated acid not to be more acidic than hydrohalic acids.

These salts, acting as catalysts, can be introduced preformed or can be prepared in situ by neutralization of an oxide of the element M, by mixing salts of the element M, or displacement of a weaker or more volatile acid by said superacid ZH. However, the in situ events generally give inferior results to the salt synthesized beforehand.

According to the present invention, the reaction for the formation of urethane and in particular of polyurethane can be a transcarbamation reaction. This term of transcarbamation should be taken lato sensu, that is to say that it is also targeted at the conversion of a pseudocarbamate (reaction product of an isocyanate with a hydroxylated derivative not constituting an alcohol, for example chosen from oximes or hydroxyamides) to a urethane or polyurethane by condensation with an alcohol or more generally with a polyol known in the field.

These catalysts are advantageously used in an amount at least equal to 0.5‰ and at most equal to 5% as carbamate functional group equivalent, preferably between 1‰ and 2%.

The transcarbamation reaction depends on the alcohols and carbamates used. However, it is between 100 and 200° C., preferably between 120 and 180° C. The carbamates used are those resulting from the reaction of an isocyanate functional group with a hydroxyl functional group. Mention should be made, among hydroxyl functional groups, of alcohol functional. groups, in particular those of alcohols which are volatile at the reaction temperature (boiling point at atmospheric pressure) and more paticularly methanol.

Among the other hydroxyl functional groups which may be mentioned as exhibiting a specific advantage, phenol functional groups, hydroxyl functional groups grafted to a nitrogen atom, such as hydroxyimides, or oximes.

The alcohols which are substituted for these hydroxylated derivatives are advantageously polyols (especially di- and/or triols), advantageously primary polyols.

The molecular masses can vary within a wide range according to the form of the coating used. The molecular masses are relatively high, it being possible for them to range approximately up to 20 000 when the catalysts according to the present invention are employed in a powder paint. On the other hand, for more conventional applications, the polyols rarely exceed a molecular mass of approximately 3 000.

The molecular masses referred to are number-average molecular masses Mn and are defined by the gel permeation technique known to "a person skilled in the art". More specifically, the molecular mass is determined by gel permeation chromatography (GPC). The technique uses two polystyrene gels (Ultrastyrogel® at $10^4$ and 500 Å) as gels, THF as solvent and sulfur as standard.

The isocyanates giving rise or corresponding to the carbamates which are preferred are at least partially aliphatic isocyanates, that is to say that the isocyanate functional group under consideration is connected via the nitrogen to the backbone of the isocyanate molecule by a carbon atom possessing $sp^3$ hybridization.

In addition, it is desirable, in the structure of the isocyanate monomer or monomers (that is to say, the isocyanates, generally diisocyanates, which constitute the precursors of the isocyanates used as "crosslinking agents", the most commonly used of which are hexamethylene diisocyanate and the compound denoted by the term isophorone diisocyanate, or IPDI), for the part of the backbone connecting two isocyanate functional groups to comprise at least one polymethylene sequence $(CH_2)_\pi$ where $\pi$ represents an integer from 2 to 10, advantageously from 4 to 8. This preference affects the mechanical performance.

When there are several sequences, the latter can be alike or different. In addition, it is desirable, in the monomer under consideration, for these polymethylene sequences to be free to rotate and therefore exocyclic, if there is a ring. When prepolymers, or oligomers, resulting from more than one monomer are used, it is desirable for the condition relating to this polymethylene sequence to be found in at least one of these monomers.

The preferred polyisocyanates are those which exhibit at least one aliphatic isocyanate functional group. In other words, at least one masked isocyanate functional group according to the invention is connected to the backbone via a carbon of $sp^3$ type advantageously carrying a hydrogen atom, preferably two. It is desirable for said carbon of $sp^3$ type to be itself carried by a carbon of $sp^3$ type advantageously provided with one and preferably two hydrogen atoms, this being in order to avoid the isocyanate group under consideration being in the neopentyl position.

In other words, it is advisable to choose, as monomer (which monomers generally carry two isocyanate functional groups), at least one compound which carries at least one aliphatic isocyanate functional group which is neither secondary nor tertiary, nor neopentyl.

In the case of a mixture obtained from several (in general two) types of monomers, it is preferable for that or those of the monomers which correspond to the above conditions and/or (advantageously "and") to the condition with regard to the presence of polymethylene sequence $(CH_2)_\pi$ to represent at least ⅓, advantageously ½, preferably ⅔, of the masked isocyanate functional groups. Thus, during the study according to the present invention, excellent results were obtained with mixtures comprising ⅔ of HMDT (hexamethylene diisocyanate "trimer") with IPDI or IPDT (IPDI "trimer"), the two being masked according to the invention (nBDI, norbornane diisocyanate, and its trimer are similar).

Of course, preference is given to the case where all the isocyanates are aliphatic and also correspond to the above criteria.

According to the present invention, the masked isocyanate, pure or as a mixture, results from a polyisocyanate, that is to say having at least two isocyanate functional groups, advantageously more than two (possibilities of fractional values since it generally relates to a mixture of more or less condensed oligomers), which itself generally results from a precondensation or from a prepolymerization of an individual diisocyanate (sometimes described as "monomer" in the present description).

The average molecular mass of these prepolymers or of these precondensates is generally at most equal to 2 000 (one significant figure), more commonly to 1 000 (one significant figure, preferably two).

Thus, among the polyisocyanates used for the invention, mention may be made of those of the biuret type and those for which the di- or trimerization reaction has resulted in four-, five- or six-membered rings. Among the six rings, mention may be made of the isocyanuric rings resulting from a homo- or hetero-trimerization of various diisocyanates alone, with other isocyanate(s) [mono-, di- or polyisocyanate(s)] or with carbon dioxide gas; in this case, a nitrogen of the isocyanuric ring is replaced by an oxygen. The oligomers comprising isocyanuric rings are preferred.

Mention should be made, among the most advantageous monomers, of those which exhibit a polymethylene sequence as defined above which is exocyclic, obviously including noncyclic. Mention may be made, among monomers exhibiting a polymethylene sequence, of tetramethylene diisocyanate optionally substituted by an alkyl group, advantageously of at most four carbon atoms, preferably of at most two carbon atoms; pentamethylene diisocyanate optionally substituted by an alkyl group, advantageously of at most four carbon atoms, preferably of at most two carbon atoms, and hexamethylene diisocyanate. Mention may be made, as monomers of cycloaliphatic nature which are preferably used in combination with isocyanates having exocyclic or noncyclic polymethylene sequences, of the monomers and the compounds resulting from the monomers below:

→ the compounds corresponding to the hydrogenation of the aromatic ring or rings carrying the isocyanate functional groups of aromatic isocyanate monomers, and in particular TDI (toluene diisocyanate) and biphenyl diisocyanates, the compound known under the abbreviation $H_{12}MDI$ and the various BICs [bis(isocyanatomethylcyclohexane)]; and especially → norbornane diisocyanate, often known by its abbreviation NBDI;

→ isophorone diisocyanate or IPDI or 3-isocyanato-methyl-3,5-trimethylcyclohexyl isocyanate.

It should be pointed out that the catalysts according to the present invention are also favorable when the reaction for the formation of urethane comprises a reaction in which a urea functional group is converted to a carbamate functional group. The urea functional group (>N—CO—N<) should be taken within the broad sense and is targeted especially at the compounds which constitute isocyanates masked by derivatives, or more specifically masking agents, carrying a reactive hydrogen on a nitrogen. These masked isocyanates make it possible to result in polyurethanes by means of alcohols and in particular of polyols.

The notion of masking agent corresponds to that which has formed the subject of studies such as that of Petersen and that of Wicks.

The present invention is of particular use for the masked isocyanates for which the release temperature, as defined in the octanol test (see below), is relatively high, that is to say at least equal to 100° C., advantageously to 120° C., preferably to 130° C.

The masking agents giving the best results are the masking agents exhibiting an NH functional group. Thus, advantageously, the masking agent, or at least one of them when there is more than one of them, is chosen from the compounds exhibiting an >NH functional group, advantageously from secondary amines or five-membered aromatic nitrogenous rings preferably exhibiting at least two nitrogens.

However, those which are chosen from compounds carrying hydroxylated functional groups advantageously chosen from saturated alcohols with a boiling point of less than 150° C. (advantageously less than 100° C.), phenols, oximes and hydroxyamide.

According to the present invention, it is desirable for the metal corresponding to the cation M not to exhibit a valency of less than 3.

It is also advantageous for the metal to be a relatively heavy metal, that is to say for said metal to belong to a period greater than the fourth period, advantageously than the fifth period. Reference may be made to the Periodic Table which forms the subject of the supplement to the Bulletin de la Société Chimique de France, No. 1, in January 1966.

The cations targeted by the present invention are essentially those of the rare earth metals (scandium, yttrium, lanthanum and lanthanide) and the elements of the Periodic Table of the Elements chosen from gallium, arsenic, indium, tin, antimony, thallium and bismuth.

Mention should be made, among the metals giving the best results, of lanthanides (lanthanide being taken here stricto sensu, that is to say that it does not comprise lanthanum), in particular yttrium and especially bismuth.

As regards the sulfonates, it is desirable for $R_x$ to be of formula:

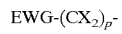

$$EWG\text{-}(CX_2)_p\text{-}$$

where:

the X groups, which are identical or different, represent a chlorine, a fluorine or a radical of formula $C_nF_{2n+1}$, with n an integer at most equal to 5, preferably to 2, with the condition that at least one of the X groups is fluorine, fluorine advantageously carried by the carbon connected to the sulfur;

p represents an integer at most equal to 2;

EWG represents an electron-withdrawing group (that is to say, $\sigma_p$ of greater than zero, advantageously than 0.1, preferably than 0.2), the possible functional groups of which are inert under the conditions of the reaction, advantageously fluorine or a perfluorated residue of formula $C_nF_{2n+1}$, with n an integer at most equal to 8, advantageously to 5, the total carbon number of Rf advantageously being between 1 and 15, preferably between 1 and 10.

As was indicated, it is preferable for the carbon carrying the sulfonate functional group to be a perfluorinated carbon and in particular a carbon constituting a perfluoromethylene (—$CF_2$—). For reasons of ease of industrial preparation, the first members of the $R_f$ (perfluoroalkyl) groups are preferred and in particular trifluoromethanesulfonic acids (triflic acid, corresponding to the triflate) and pentafluoro-ethanesulfonic acids give good results.

Another subject matter of the present invention is masked isocyanate compositions, the masked isocyanates advantageously being in the form of carbamates (lato sensu, that is to say the functional groups corresponding to the sequence —N(R)—CO—O—, where R is a hydrocarbonaceous radical, generally an alkyl radical, indeed even an aryl radical, or more commonly a hydrogen), additionally comprising a catalyst of following general formula (I):

$$MY_{3-q}[(R_x)-SO_2-O-]_q,$$

where:

M represents a trivalent metal, preferably known for forming Lewis acids;

Y is a monovalent anion or anionic functional group, and;

$R_x$ is a radical, the carbon of which carrying the sulfonic functional group is perhalogenated, and q is an integer advantageously chosen between 1 and 3, including the limits.

The present invention is also targeted at a transcarbamation process where use is made, as transcarbamation catalyst, of the compounds of formula:

$$MY_{3-q}[(R_x)-SO_2-O-]_q,$$

where:

M represents a trivalent metal, preferably known for forming Lewis acids;

Y is a monovalent anion or anionic functional group, and;

$R_x$ is a radical, the carbon of which carrying the sulfonic functional group is perhalogenated, and q is an integer advantageously chosen between 1 and 3, including the limits.

These catalysts make it possible to carry out the reaction at temperatures below 200° C., generally below 180° C.

Generally, to obtain satisfactory kinetics, it is advisable to be at a temperature at least equal to 100° C., preferably at a temperature at least equal to 120° C.

| Octanol test | |
| --- | --- |
| "Release" (or "deblocking") temperature: | This is the lowest temperature at which the masking agent of the masked isocyanate is displaced to an extent of 9/10 (rounded mathematically) by a primary monoalcohol (the primary monoalcohol is generally octanol). |
| Shelf life: | To ensure that the product has a good shelf life, it is preferable to choose masked isocyanate functional groups which show, in the octanol test, a "release" at 80° C., advantageously at 90° C., at most equal to 90%. |
| Progress of the reaction: | The reaction is considered to be complete if it is carried out to more than 90%. |

The following nonlimiting examples illustrate the invention. These examples, in order to avoid any interaction problems, related substantially to monofunctional isocyanates. n-Hexyl isocyanate was used.

EXAMPLE 1

General Procedure:

Choice of the Reaction Model

The choice focused on the use of aliphatic isocyanates, which are more expensive but which give access to polyurethanes exhibiting:
better resistance to UV radiation,
a more stable color,
excellent behavior when used externally.

The action of primary alcohols gives carbamates which are very stable thermally in comparison with aromatic isocyanates.

Methanol was chosen as blocking agent for the alkyl isocyanate. This is because this alcohol is inexpensive, has a low molecular mass and has a limited toxicity.

A limitation on volatile organic compounds (VOCs) is promoted by such a blocking agent in comparison with the other agents. This methodology clearly falls within the scope of the development of a cleaner chemistry, an approach favored by current research.

Reactants Involved

The alkyl isocyanate chosen is hexyl isocyanate. It is blocked very simply with methanol with conventional heating for 4 hours. The reaction results in the formation of N-hexyl methyl urethane, which will be used as starting reactant during the transcarbamation reaction.

n-hex-N=C=O+MeOH→n-hex-NH—CO—OMe

The primary alcohol chosen for carrying out the transcarbamation is ocatan-1-ol. The reaction of it with hexyl isocyanate with conventional heating for 4 hours results in the formation of the end product: N-hexyl octyl urethane.

n-hex-N=C=O+n-OctOH→n-hex-NH—CO—O-n-Oct

The characterization of this product by conventional analytical techniques was necessary in order to carry out kinetic monitoring of the transcarbamation reaction by gas chromatography (retention time and response factor).

Kinetic Study

The transcarbamation reaction studied, carried out in the absence of solvent and in the presence of 1 mol % of catalyst (in order to have a rapid reaction), is represented diagrammatically below:

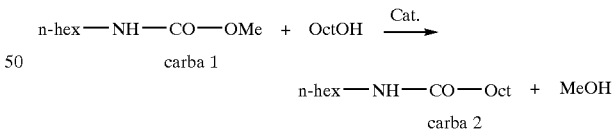

Carba 1: 3.14 mmol (500 mg)
OctOH: 1 eq. or 10 eq.
Internal reference (hexadecane): 0.5 eq.
Cat.: 1 mol %.
130° C.

Kinetic Results of Various Catalysts Tested

| Catalyst | k in $mol^{-1} \cdot l \cdot min^{-1}$ | Yield (%) |
| --- | --- | --- |
| $Bu_2Sn(laurate)_2$ reference | $1.10 \cdot 10^{-3}$ | 26 |
| $BiPh_3$ comparative | 0 | 0 |

-continued

| Catalyst | k in mol$^{-1}$ · l · min$^{-1}$ | Yield (%) |
|---|---|---|
| BiCl$_3$ comparative | 3.80 · 10$^{-5}$ | 2 |
| Bi(OTf)$_3$ | 5.54 · 10$^{-3}$ | 70 |
| Yb(OTf)$_3$ | 8.76 · 10$^{-4}$ | 30 |
| Sm(OTf)$_3$ | 2.0 · 10$^{-3}$ | 45 |

Triphenylbismuth and bismuth chloride display virtually no catalytic activity. With regard to bismuth triflate, it shows a noteworthy effectiveness with a rate constant of 4.54·10$^{-3}$ mol$^{-1}$.l.min$^{-1}$ and a final yield of 70%, a result entirely comparable with the dibrominated distanoxane.

Test Carried Out with Methyl Hexamethylenedicarbamate.

EXAMPLE 2

Synthesis of Methyl Octylcarbamate 41.44 g of 1-n-octyl isocyanate and 17 g of methanol are charged to a reactor. The mixture is stirred at 60° C. for 8 hours. The product is subsequently cooled to ambient temperature. It crystallizes. The crystallized product is filtered off (38 g). The crystallized product is washed with cold hexane to give 19 g of pure product.

The carbamate is characterized by proton HMR and infrared analysis.

EXAMPLE 3

Synthesis of Octyl Octylcarbamate

The synthesis is carried out in the same way as for example 1, from 1.7 g of 1-n-octyl isocyanate (1 molar equivalent) and 2.86 g of n-octanol (2 molar equivalents).

After 4 hours, the absence of isocyanate bands is monitored by infrared analysis. The product is purified as described above.

This product serves as reference.

The carbamate is characterized by proton HMR and infrared analysis.

EXAMPLE 4

Synthesis of Octyl Hexylcarbamate

The synthesis is carried out as for example 1, except that n-1-hexyl isocyanate (5 g) and octanol (10 g) are used.

Approximately 5 g of product are recovered.

The carbamate is characterized by proton HMR and infrared analysis.

This product serves as reference.

EXAMPLE 5

Synthesis of Methyl Hexylcarbamate

The synthesis is carried out as for example 1, except that n-1-hexyl isocyanate (5 g) and methanol (1.8 g) are used.

Approximately 5.7 g of product are recovered.

The carbamate is characterized by proton HMR and infrared analysis.

EXAMPLE 6

Conditions for Analyses of the Reaction

The transcarbamation reaction is monitored by gas chromatographic analysis using a column.

The compounds are eluted via a 100° C. to 220° C. temperature gradient with an increase of 10° C./min. The injection temperature is 100° C.

| Compound | Elution time |
|---|---|
| Octanol | 5.22 |
| Trichlorobenzene (internal reference) | 7.41 |
| Methyl hexylcarbamate | 8.32 |
| Methyl octylcarbamate | 11.14 |
| Octyl hexylcarbamate | 16.41 |
| Octyl octylcarbamate | 21 |

EXAMPLE 7

Synthesis of Methyl Hexamethylenedi-carbamate

The synthesis is carried out as for example 1. 171 g of examethylene diisocyanate and 271 g of methanol are used.

The NCO content is monitored by measuring the content by reaction with excess dibutylamine and quantitative determination of the excess dibutylamine with HCl (conventional quantitative determination of isocyanates).

The methyl dicarbamate crystallizes under cold conditions. It is washed with hexane and then dried.

$^1$H NMR analysis gives NH 4.7 ppm; —CH$_3$O 3.6 ppm; —CH$_2$N 3.1 ppm; —(CH$_2$)$_4$ 1.4 and 1.27 ppm.

General Procedure of the Tests for Transcarbamation Catalyses

The reaction is carried out at 160° C. in a stirred reactor with 1 molar equivalent of methyl carbamate and 1 molar equivalent of octan-1-ol. 1 mol % of catalyst is added.

EXAMPLE 8

Transcarbamation Reaction Catalyzed by Metal Triflates at 160° C.

| Starting methyl carbamate used | Catalyst used/ temperature/ reaction for 4 hours | Degree of conversion of the methyl carbamate to octyl carbamate |
|---|---|---|
| Methyl octyl-carbamate | La(Triflate)$_3$/160° C. | 62% |
| Methyl octyl-carbamate | Yb(Triflate)$_3$/160° C. | 99% |

EXAMPLE 9 (COMPARATIVE)

Transcarbamation Reaction Catalyzed by Metal Triflimides at 160° C.

| Starting methyl carbamate used | Catalyst used/ temperature/ reaction for 4 hours | Degree of conversion of the methyl carbamate to octyl carbamate |
|---|---|---|
| Methyl octyl-carbamate | Potassium bis(trifluoro-methanesulfonimide)/160° C. | 42% |
| Methyl octyl-carbamate | Lithium bis(trifluoro-methanesulfonimide)/160° C. | 51% |
| Methyl octyl-carbamate | Magnesium bis(trifluoro-methanesulfonimide)/160° C. | 45% |

The mixtures of catalysts prepared in situ proved to be less efficient than the derivatives prepared before the reaction.

EXAMPLE 10

Transcarbamation Reaction Catalyzed by Mixtures of Metal Salts at 160° C.

| Starting methyl carbamate used | Catalyst used/ temperature/ reaction for 4 hours | Degree of conversion of the methyl carbamate to octyl carbamate |
|---|---|---|
| Methyl octyl-carbamate | 1 molar eq. triflic acid + 1 molar equivalent $BiCl_3$/130° C. | 33% |
| Methyl octyl-carbamate | 2 molar eq. triflic acid + 1 molar equivalent $BiCl_3$/130° C. | 29% |
| Methyl octyl-carbamate | 3 molar eq. triflic acid + 1 molar equivalent $BiCl_3$/130° C. | 34% |
| Methyl octyl-carbamate | 1 molar eq. bis(tri-fluoromethanesulfon)-imide (TFSIH) + 1 molar equivalent $BiCl_3$/130° C. | 28% |
| Methyl octyl-carbamate | 2 molar eq. TFSIH + 1 molar equivalent $BiCl_3$/130° C. | 20% |
| Methyl octyl-carbamate | 3 molar eq. TFSIH + 1 molar equivalent $BiCl_3$/130° C. | 25% |
| Methyl octyl-carbamate | 1 molar eq. triflic acid + 1 molar equivalent $Bi_2O_5$/130° C. | 39% |

EXAMPLE 11

Transcarbamation Reaction of methyl hexa-methylenedicarbamate and Diol or Polyoldiol Compounds The reaction is carried out in the presence of the best catalysts obtained. It is confirmed whether a gel is obtained. The degree of conversion of the methyl hexamethylenedicarbamate is measured by extraction with a polar solvent, N-methylpyrrolidone, and quantitative determination by GC. It is shown that, in all cases, the amount of dimethyl hexamethylenecarbamate is less than 10%.

These examples show that it is possible to obtain polyurethanes by a transcarbamation reaction catalyzed by the organometallic derivatives of the invention.

| Starting methyl carbamate used/polyol NCO/OH ratio = 1 | Catalyst used/ temperature/reaction for 4 hours | Qualitative result |
|---|---|---|
| Methyl hexamethylenedi-carbamate/hexane-1,6-diol | Yb(triflate)$_3$/160° C. | Production of a gel |
| Methyl hexamethylenedi-carbamate/hexane-1,6-diol | Bi(triflate)$_3$/160° C. | Production of a gel |
| Methyl hexamethylenedi-carbamate/hexane-1,6-diol | Bi(triflate)$_3$/130° C. | Production of a gel |
| Methyl hexamethylenedi-carbamate /polyethylene glycol mass 1 000 | Yb(triflate)$_3$/160° C. | Production of a gel |

COMPARATIVE EXAMPLES 12

Transcarbamation Reaction Catalyzed by Protic Acids

The reaction is carried out at 160° C. in a stirred reactor with 1 molar equivalent of methyl carbamate and 1 molar equivalent of octan-1-ol. 1 mol % of acid catalyst is added. The reaction mixture is left to stir under sealed conditions.

The results are analyzed after 6 hours at 160° C. and 130° C. by gas chromatography.

The transcarbamation levels measured are low in comparison with those measured with the Lewis acids.

| Starting methyl carbamate used | Catalyst used/ temperature | Mol % of octyl carbamate measured |
|---|---|---|
| Methyl octyl-carbamate | Triflic acid/160° C. | 8% Octyl octyl-carbamate |
| Methyl octyl-carbamate | Bis(trifluoro-methanesulfon)-imide/160° C. | 5.6% Octyl octyl-carbamate |
| Methyl hexyl-carbamate | Triflic acid/160° C. | 10% Octyl octyl-carbamate |
| Methyl hexyl-carbamate | Bis(trifluoro-methanesulfon)-imide/160° C. | 6% Octyl octyl-carbamate |

The invention claim is:

1. A process for the formation of urethane through a transcarbamation reaction, comprising the steps of:
   a) carrying out said reaction on a mixture of a carbamate, said carbamate resulting from the reaction of of an isocyanate functional group with a hydroxyl functional group, and an alcohol in the presence of an efficient catalytic amount, as catalyst for a reaction for the formation of urethane, of compounds of general formula (I):

   $MY_{3-q}[Z]_q$, wherein:
   Z is the radical corresponding to the anion of a superacid for which the Hammett constant is at least equal to, or greater than, 13;
   M representing a trivalent metal;
   Y is a monovalent anion or anionic functional group: and
   q is an integer; and
   b) recovering the urethane formed in step a).

2. The process according to claim 1, wherein:
the Hammett constant is greater than 13;
M forms a Lewis acid; and
q is between 1 and 3, including the limits.

3. The process according to claim 1, wherein Z is of formula:

$(R_x)-SO_2-\zeta-$ wherein:
$R_x$ is a fluorine or a radical, the carbon of which carrying the sulfonic functional group is perhalogenated, and
$\zeta$ is an oxygen or an atom from Group V, monosubstituted by an electron-withdrawing radical.

4. The process according to claim 3, wherein:
$\zeta$ is an oxygen or nitrogen, monosubtituted by the electron-withdrawing radical of formula $(R'_x)-SO_2-$, wherein $R'_x$ are radicals $R_x$.

5. The process according to claim 4, wherein $\zeta$ is an oxygen.

6. The process according to claim 1, wherein the transcarbamation comprises a reaction in which a urea functional group (>N—CO—N<) is converted to a carbamate functional group (>N—CO—O—).

7. The process according to claim 6, wherein a precursor of the urethane functional group is a masked isocyanate functional group with a masking agent.

8. The process according to claim 7, wherein the masking agent is a compound carrying a hydroxylated functional group.

9. The process according to claim 8, wherein the compound carrying a hydroxylated functional group is a saturated alcohol with a boiling point below 150° C., phenol, oxime or hydroxyamide.

10. The process according to claim 7, wherein the masking agent is a compound exhibiting an >NH functional group.

11. The process according to claim 10, wherein the compound exhibiting an >NH functional group is a secondary amine or a five-membered aromatic nitrogenous ring, optionally exhibiting at least two nitrogens.

12. The process according to claim 1, wherein said metal M is a metal not exhibiting a valency of less than 3.

13. The process according to claim 12, wherein said metal belongs to a period greater than the fourth, optionally than the fifth, period.

14. The process according to claim 13, wherein said metal is a lanthanide or bismuth.

15. The process according to claim 1, wherein $R_x$ is of formula:

$EWG-(CX_2)_p-$ wherein:
the X groups, which are identical or different, represent a chlorine, a fluorine or a radical of formula $C_nF_{2n+1}$, with n an integer at most equal to 5, with the further proviso that at least one of the X groups is fluorine, said fluorine being carried by the carbon connected to the sulfur;
p represents an integer at most equal to 2; and
EWG represents an electron-withdrawing group inert under the conditions of the reaction.

16. The process according to claim 15, wherein EWG has fluorine or a perfluorinated group of formula $C_nF_{2n+1}$, with n an integer at most equal to 8, the total carbon number of Rf being between 1 and 15.

17. The process according to claim 1, wherein the transcarbamation reaction of step a) is carried out at a temperature of between 100 and 200° C.

18. The process according to claim 1, wherein the amount of catalyst is at least equal to 0.5% and at most equal to 5% as carbamate functional group equivalent.

* * * * *